United States Patent [19]
Rakitsky et al.

[11] Patent Number: 5,175,277
[45] Date of Patent: Dec. 29, 1992

[54] RAPIDLY HYDRATING WELAN GUM

[75] Inventors: Walter G. Rakitsky; Danny D. Richey, both of San Diego, Calif.

[73] Assignee: Merck & Co., Inc., Rahway, N.J.

[21] Appl. No.: 672,505

[22] Filed: Mar. 20, 1991

[51] Int. Cl.$^5$ .............................. C08B 37/00
[52] U.S. Cl. .................. 536/114; 536/4.1; 536/119; 536/123; 106/729
[58] Field of Search ............ 536/114, 1.4, 119

[56] References Cited

U.S. PATENT DOCUMENTS

| | | | |
|---|---|---|---|
| 2,526,674 | 10/1950 | Larsen et al. | 106/718 |
| 3,432,317 | 3/1969 | Kelly et al. | 106/729 |
| 4,073,658 | 2/1978 | Ohtani et al. | 106/729 |
| 4,095,987 | 6/1978 | Walker | 209/241 |
| 4,342,866 | 8/1982 | Kang et al. | 536/119 |
| 4,963,668 | 10/1990 | Allen et al. | 536/124 |

FOREIGN PATENT DOCUMENTS 1425822  2/1976  United Kingdom .

Primary Examiner—Johnnie R. Brown
Assistant Examiner—Pamela S. Webber
Attorney, Agent, or Firm—Richard S. Parr; Charles M. Caruso

[57] ABSTRACT

A rapidly hydrating welan gum useful for preparing cementitious products. The gum can be dry blended with cement or other dry component and then added to a preformed cement/water pre-mix, thereby alleviating the need for hydrating the gum prior to addition to a cement/water mixture.

1 Claim, No Drawings (1)

RAPIDLY HYDRATING WELAN GUM

BACKGROUND OF THE INVENTION

Concrete compositions contain aggregate (e.g., sand and rock), cement and water. When water is added to the cement, a paste forms which hardens over time to a solid structure. Various additives have been used in cement compositions to modify their properties. Long fibers such as asbestos reduce the sagging of these pastes and thus is beneficial when applying tiles to a vertical surface. Freezing point depressants are used when cements are to be poured in subfreezing temperatures. Bentonite clay has been used for this purpose. Other polymers, such as the polyvinyl alcohols and methyl methacrylates, have been used to reduce friction when pumping these pastes and to otherwise modify their workability. Fumed silica is used as an additive to make stronger concrete with reduced permeability.

U.S. Pat. No. 4,963,668 describes cement compositions comprising 0.01 to 0.9% welan gum by weight of dry cement to improve workability, suspension of aggregates, air entrainment, sag resistance, flow characteristics and resistance to water loss.

Incorporation of fluid-enhancing polymeric material into cement-containing mixtures is difficult when the fluid-enhancing material requires hydration. Such hydration must be achieved by lowering the initial amount of water used to mix the cement and sand, hydrating the polymer with water, and then adding the polymer/water dispersion to the initial cement/sand/water mix to obtain a cement/sand/water/polymer mixture having the desired final weight ratio.

When water is held out of the concrete to hydrate the polymer, the amount of water which can be used to initially disperse cement and sand is insufficient to form a uniform mix. Large golf and bowling ball-size agglomerates form which do not disperse even when the balance of the mixing water is added. Furthermore, pre-hydration of the polymer does not occur quickly enough to stay in synchronization with the typical 60-90 second batch plant mixing cycle. It is also impractical to have a large quantity of hydrated polymer solution available for inclusion into the concrete without significant additional costs for preservation, mixing, and storage.

Addition of water containing hydrated polymer to a dry cement/sand mixture such that the desired cement-/sand/water/polymer weight ratio is achieved immediately is undesirable because the polymer can interfere with early stages of cement hydration and may impair mechanical properties of the mixture. Such addition also makes dispersion of the cement particles more difficult.

The present invention is a rapidly hydrating welan gum useful for improving cement workability. The gum is an improvement over the prior art because predispersion/prehydration of the gum prior to mixing with concrete is not required in order to obtain a uniform, workable mix.

SUMMARY OF THE INVENTION

The invention is a rapidly hydrating welan gum which is useful for situations where welan gum addition in a pre-hydrated dispersion form is not pratical.

The gum has hydration characteristics sufficient for it to be dry blended with cement and other chemical additives or admixture such as an air entraining agent, corrosion inhibitor, accelerator or retarder, or as a dispersion in a carrier which is typically a superplasticizer (dispersant), and then added to a preformed cement-/water pre-mix. The preformed cement/water pre-mix may also contain aggregate (e.g. sand and rock) sufficient for concrete composition formation. The polymer does not swell and generate viscosity in the carrier which makes it a convenient way to add welan gum to cementitious products. Because of its enhanced hydration properties, the polymer is able to achieve full functionality under field make-up conditions. Typical batch plant mixing cycles are from 60-120 seconds at relatively low shear rates.

DETAILED DESCRIPTION OF THE INVENTION

Welan gum describes an industrial grade of a microbial polysaccharide produced by the growth of the Alcaligenes strain ATCC 31555 in a pure culture fermentation using carbohydrates as a carbon source. The product is recovered from the fermentation broth by precipitation with alcohol. Welan gum is a polysaccharide gum which comprises principally a heteropolysaccharide containing the neutral sugars D-glucose, D-glucuronic acid, L-rhamnose and L-mannose and glycosidically linked acetyl ester groups. The structure of this polysaccharide is described in Jansson P E, Lindberg B, and Widmalm G (1985) *Carbohydrate Research* 139, 217-223.

The rapidly hydrating welan gum used in the present invention is a novel form of welan gum. Kang et al., U.S. Pat. No. 4,342,866, describes a procedure for making welan gum that does not have hydration characteristics such as those of the rapidly hydrating welan gum of the present invention.

Preparation of rapidly hydrating welan gum

This gum is prepared by a procedure which includes many of the steps used to prepare welan gum described in U.S. Pat. No. 4,342,866 (the welan gum hereinafter referred to as "welan gum S-130"), i.e., S-130 fermentation followed by precipitation, drying and milling. However, the welan gum useful in the present invention is obtained by modification of the S-130 process. The modification involves adjustment of the fermentation broth, prior to precipitation, to a pH of between about 10.5 and 12.5, preferably with KOH or soda ash, more preferably 45% KOH, followed by heating between about 170° F. and 230° F. for approximately 3-20 minutes. Precipitation followed by drying and milling occur in the normal manner. Preferably, the pH is adjusted to between about 11 and 11.5, and the broth is heated for about 5 minutes at 210° F. It is also preferable to add calcium propionate, more preferably 0.2%, to the broth before pH adjustment.

Description of the Strains used for producing rapidly hydrating welan gum

A. Characteristics of Colonial Morphology

On nutrient agar, small yellow colonies appear in one day at 30° C. with the diameter reaching about 1.5 mm after 5 days' incubation. The colonies are round, smooth, convex, mucoid, and opaque. The yellow color becomes more deep and the texture of colonies becomes hard after prolonged incubation.

On YM agar, small mucoid yellow colonies appear in one day and the diameter reaches about 3 mm after 5 days' incubation. The colonies are round, smooth, convex, and opaque, but the top of the colonies are flat. No membraneous hard texture is observed.

B. Characteristics of Cell Morphology

Strain S-130 is a gram-negative rod-shaped bacterium. On nutrient agar the average size of the cell is about 0.5-0.6 by 1.2-1.6 μm; ends of the cells are tapered and curvature was often seen. The size and shape of the cells do not change significantly after prolonged incubation.

On YM agar the average cell size is 0.6-0.8 by 1.6-2.0 μm, but the cell becomes longer (3-4 μm); accumulation of PHB is significant. Motility is positive. Flagella stains (modified silver nitrate method) show that the strain has mixed flagellation, i.e., polar and lateral flagella, as well as peritrichous flagella.

C. Physiological and Biochemical Characteristics

The following are results of tests employed:

Cytochrome oxidase is weak or negative; catalase positive.

Organism is capable of growth at 37° and 41° C., but not at 43° C.

Tolerance to 3.0% NaCl, but not to 6.5% NaCl.

Growth at pH between 5 and 12.

Aerobic acid but not gas was produced from various carbohydrates, such as:

| | |
|---|---|
| D-xylose | lactose |
| L-arabinose | maltose |
| D-glucose | melibiose |
| fructose | sucrose |
| galactose | trehalose |
| mannose | raffinose |

Litmus milk was reduced, but not peptonized.
ADH was positive, but not LDC, ODC, and PDA.
MR positive, but negative for VP, indole, and urease.
Esculin gelatin (weak) and Tween 80 (weak) were hydrolyzed, but not casein, starch, cellulose, pectin.
No phosphatase, and haemolysis negative.
0.1% triphenyltetrazolium chloride was not inhibitory.
Survival at 60° C. for 30 minutes.
Organisms grow on EMB agar and Tellurite Blood, but not on SS and MacConkey agar.

D. Antibiotic Susceptibility Test

The strain S-130 is susceptible to the following antibiotics.

| | |
|---|---|
| Kanamycin | 30 μg |
| Neomycin | 30 μg |
| Chlortetracycline | 5 μg |
| Novobiocin | 30 μg |
| Erythromycin | 15 μg |
| Tetracycline | 30 μg |
| Gentamicin | 10 μg |
| Carbenicillin | 50 μg | and not susceptible to:

| | |
|---|---|
| Penicillin | 10 units |
| Streptomycin | 10 μg |
| Colistin | 10 μg |
| Polymyxin B | 300 units |

E. Nutritional Characteristics

Organic growth factors are not required and ammonium salts serve as the sole nitrogen source. A total of 30 organic compounds are utilized as sole source of carbon and energy. Most carbohydrates are utilized.

F. G+C Content of the DNA

No DNA analysis was performed.

G. Identification by API System

The strain could not be identified by this system.

H. Identification

The strain S-130 is a gram-negative aerobic rod-shaped organism. The mode of flagellation of the organism is mixed; polar and peritrichous flagella (possibly degenerate flagella) are seen. According to Bergey's Manual (8th Edition), such organisms belong as a member of the genus Alcaligenes.

TABLE I

Biochemical and Other Miscellaneous Tests Employed for the Strain S-130

| | |
|---|---|
| Oxidase: Kovac's | + (weak) |
| Pathotech | + (weak) |
| Catalase | + |
| OF medium: | |
| Oxidative | + |
| Fermentative | − |
| Gas from glucose | − |
| H₂S production | − |
| TSI from cystine | ± |
| Ammonium from peptone | NT |
| β-Galactosidase (ONPG) | − |
| Argnine dihydrolase | + |
| Lysine decarboxylase | − |
| Ornithine decarboxylase | |
| Tryptophan deaminase | NT |
| Phenylalanine deaminase | − |
| Urease | − |
| Indole | − |
| MR test | + |
| VP test | − |
| Nitrate reduction | − |
| Nitrite reduction | − |
| Denitrification | NT |
| N₂-fixation: | |
| Growth in Burk's medium | + |
| Nitrogenase activity | NT |
| Melonate (oxidation) | − |
| Phosphatase | − |
| Haemolysis (sheep blood) | − |
| Litmus milk: acid, reduction only | − |
| 3-ketolactose production | |
| Survival at 60° C. for 30 min. | + |
| TSI: Slant | Acid |
| Butt | No growth |
| Gas | − |
| Egg Yolk Reaction | − |
| Hydrolysis of: | |
| Gelatin | + (weak) |
| Casein | − |
| Starch | − |
| Tween 80 | + (weak) |
| Pectin | − |
| Alginate | NT |
| Cellulose | − |
| Chitin | − |
| DNA | NT |
| Esculin | + |
| Growth on various media: | |
| EMB agar | + |
| MacConkey agar | − |
| SS agar | − |
| Mannitol salt agar | − |
| TCBS agar | − |
| Tinsdale tellurite blood agar | + |
| Pseudosel agar | NT |
| Pigment production: | |

TABLE I-continued

Biochemical and Other Miscellaneous Tests Employed
for the Strain S-130

| King A medium | − |
|---|---|
| King B medium | − |
| Dye reaction: | |
| Congo red | − |

+ = positive
− = negative
NT = not tested

Fermentation conditions

Heteropolysaccharide is produced during the aerobic fermentation of suitable aqueous nutrient media under controlled conditions via inoculation with the organism of the unnamed Alcaligenes species. The media contain sources of carbon, nitrogen and inorganic salts.

In general, carbohydrates (for example, glucose, fructose, maltose, sucrose, xylose, mannitol and the like) can be used either alone or in combination as sources of assimilable carbon in the nutrient medium. The exact quantity of the carbohydrate source of sources utilized in the medium depends in part upon the other ingredients of the medium but, in general, the amount of carbohydrate usually varies between about 2% and 5% by weight of the medium. Preferably 3% glucose is used. These carbon sources can be used individually, or several such carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn steep liquor, distiller's solubles and the like. The sources of nitrogen, either alone or in combination, are used in amounts ranging from about 0.05% to 0.5% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the media described in the examples are merely illustrative of the wide variety of media which may be employed, and are not intended to be limitative.

As an alternative medium, S-130 may be grown under low Ca++ conditions, i.e., in deionized water, or some other aqueous system substantially free of Ca++ (i.e., less than about 4 ppm Ca++ per 1% gum in the final fermentor broth).

The fermentation is carried out at temperatures ranging from about 25° C. to 35° C.; however, for optimum results it is preferable to conduct the fermentation at temperatures of from about 28° C. to 35° C. The pH of the nutrient media for growing the Alcaligenese culture and producing the polysaccharide S-130 can vary from about 6 to 8, preferably 6.5 to 7.5.

A small scale fermentation is conveniently carried out by inoculating a suitable nutrient medium with the culture, and after transfer to a production medium permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources.

The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferably to conduct the fermentation in suitable tanks provided with an agitator and a means of aerating the fermentation medium. According to this method, the nutrient medium is made upin the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the heteropolysaccharide is particularly suited for the preparation of large quantities.

Post-fermentation

After fermentation, calcium propionate is preferably added to the fermentation broth, and the fermentation broth is adjusted to a pH of between about 10.5 and 12.5 with KOH or soda ash, preferably 45% KOH. pH adjustment is followed by heating between about 170° F. and 230° F. for approximately 3-20 minutes. Preferably, the pH is adjusted to between about 11 and 11.5, and the broth is heated for about 5 minutes at 210° F., and amount of calcium propionate added is about 0.2%.

After the adjustment period, the gum is precipitated using a suitable alcohol such as isopropanol. The precipitate is dried in typical fashion.

After drying, the product is milled according to standard milling procedures. Target mesh size varies according to desired product characteristics. For example, larger mesh size material, e.g. 80 mesh, is preferred for transport of the material using conventional dry material handling systems. Smaller mesh size material, e.g. 140 mesh, is preferred for enhanced rapid hydration performance. In all cases, however, the gum produced according to the described procedure, using described fermentation broth pH adjustment and subsequent heating steps, possesses rapid hydration characteristics as compared to conventionally prepared welan gum produced according to the procedure described in U.S. Pat. No. 4,342,866.

Analysis

Glucuronic acid was identified by using the method of Bhatti et al., *Biochim. Biophys. Acta* 22 (1970) 339-347. Absolute configurations of the sugars were determined by the methods devised by Gerwig et al., *Carbohydrate Research* 77 (1979) 1-7, and by Leontein et al., *Carbohydrate Research* 62 (1978) 359-362.

Methylation analyses were performed essentially as described in Jansson et al., *Chem. Common. Univ. Stockholm*, 8 (1976) 1-75. Methylated polymers were recovered by dialysis against water, followed by freeze-drying. Low-molecular-weight products were recovered by reversed phase chromatography on Sep-Pak C₁₈ cartridges, Waeghe et al., *Carbohydrate Research* 123 (1983) 281–304. The sample was diluted with an equal volume of water and applied to the column. This was washed with water and acetonitrile-water (15:85), and the sample was eluted with acetonitrile.

Carboxyl-reduction of methylated polysaccharide

The methylated polysaccharide (1.5 mg) was dissolved in freshly distilled tetrahydrofuran (2 mL). Lithium borohydride (10 mg) was added and the solution boiled under reflux for 2 hours. Excess of lithium borohydride was decomposed with M acetic acid, chloroform (5 mL) was added, and the solution was washed several times with water, dried, and concentrated.

Uronic acid-degradation

To a solution of the methylated polysaccharide (1.5 mg) in dimethyl sulfoxide (1.5 mL) were added a trace of toluene-p-sulfonic acid and 2,2-dimethoxypropane (0.1 mL) in order to eliminate any water present. Sodium methylsulfinylmethanide in dimethyl sulfoxide (2M, 1 mL) was added, and the mixture was agitated in an ultrasonic bath for 30 minutes and kept at room temperature for 15 hours. Trideuteriomethyl iodide (0.5 mL) was added with external cooling and the mixture agitated in the ultrasonic bath for 30 minutes. The excess of methyl iodide was removed by flushing with nitrogen, and the solution was diluted with water and added to a Sep-Pak C₁₈ cartridge. The material was recovered as described above. The product was hydrolyzed with 2M trifluoroacetic acid for 15 hours at 100° C. and the mixture of methylated products was analyzed (Table II, column C).

Approximately 50% of the rapidly hydrating welan gum polysaccharide units contain an O-acetyl group. An acid hydrolysate of the fermented polysaccharide contained glucose, rhamnose and mannose in the relative proportions 43:46:11. It further contained glucuronic acid, identified by g.l.c. of a sample that had been methanolyzed and trimethylsilylated using the procedure described by Bhatti et al.

Absolute configurations of component sugars were determined by g.l.c. of the glycosides obtained on solvolysis with chiral 2-butanol followed by trimethylation, as devised by Gerwig et al. The glucose and glucuronic acid have the D configuration and the rhamnose has the L configuration. The mannose has the L configuration. This was confirmed by g.l.c. of the glycosides obtained on solvolysis with chiral 2-octanol followed by acetylation, as devised by Leontein et al.

Methylation analysis without and with carboxyl-reduction of the methylated polysaccharide, gave the products listed below, columns A and B respectively.

TABLE II

METHYLATION ANALYSIS OF THE POLYSACCHARIDE AND SOME DEGRADATION PRODUCTS[a]

| Sugar[b] | T[c] | A | B | C | D | E |
|---|---|---|---|---|---|---|
| 1,2,3,5-Rhamnitol | 0.38 | | | | 13 | 22 |
| 2,3,4-Rha | 0.59 | 12 | 7 | 16 | | |
| 2,3-Rha | 0.94 | 26 | 21 | 18 | | |
| 2,3,4,6-Glc | 1.00 | | | | 54 | 36 |
| 2,3,4,6-Man | 1.00 | 10 | 7 | 19 | | 5 |
| 2,4,6-Glc | 1.67 | 26 | 23 | 43[d] | | |
| 2,3,6-Glc | 1.92 | | | | 33 | 34 |
| 2,6-Glc | 2.79 | 26 | 23 | 4 | | 3 |
| 2,3-Glc | 3.56 | | 19 | | | |

[a] Key: A, methylated polysaccharide; B, methylated and carboxyl-reduced polysaccharide; C, uronic acid-degraded polysaccharide; D, acidic tetrasaccharide; E, acidic penta- and tetra-saccharide.
[b] 2,3,4-Rha=2,3,4-tri-O-methyl-L-rhamnose, etc.
[c] Retention time of the corresponding alditol acetate, relative to 1,5-di-O-acetyl-2,3,4,6-tetra-O-methyl-D-glucitol on an SP-1000 glass-capillary column at 200° C.
[d] >90% Trideuteriomethyl at O-4.

In order to determine the sequence of the sugar residues, the rapidly hydrating welan gum polysaccharide was subjected to a uronic acid-degradation (Lindberg et al. *Carbohydrate Research* 28 (1973) 351–357 and Aspinall et al. *Carbohydrate Research* 57 (1977) c23–c26). The fully methylated polysaccharide was treated with sodium methylsulfinylmethanide in dimethyl sulfoxide, methylated (using trideuteriomethyl iodide), and hydrolyzed, and the mixture of methylated sugars was analyzed (Table II, column C). 2,6-di-O-methyl-4-O-trideuteriomethyl-D-glucose was derived from the branching D-glucopyranosyl residue, the 4-position of which was liberated on degradation of the uronic acid. The 3-substituted D-glucopyranosyl residue linked to O-4 of the uronic acid was released by β-elimination and further degraded by β-elimination, with release of the 4-substituted L-rhamnopyranosyl residue. A considerable part of this residue was also degraded.

The polysaccharide imparts viscosity to an aqueous medium when dissolved in water in low concentrations. Because of this, its sensitivity to shear and overall rheology, it is useful as a thickening, suspending, emulsifying, stabilizing, lubricating, film-forming, or binding agent, especially in aqueous systems. In particular, it has uses in the following applications or products: adhesives, wall-joint cements, grouts and mortars, spackling compounds, can sealing, boiler compounds, latex creaming, welding-rod fluxes, brazing pastes, ceramic glazes and extrusions, cleaners and polishes, toys, emulsions (latex, asphalt, silicone), silver recovery, seed coatings, spray control for pesticides or herbicides, emulsifiable concentrated and flowable pesticides and herbicides, tobacco binders, water-based inks, lithographic fountain solutions, leather finishes, hydro-mulching and hydro-seeding, textile printing and finishing, wet-end paper additives, wet-end paper retention and formation aid, anti-stick compounds, mold-release agents, liquid resins, slurry and packaged explosives, petroleum and water-well drilling muds, petroleum workover and completion fluids, petroleum stimulating fluids, fracturing, spacer fluids, gravel packing cosmetics, pharmaceutical suspensions and emulsions.

EXAMPLE 1

Fermentation and Recovery Procedure for Producing Rapidly Hydrating Welan Gum

A. Culture Maintenance

The unnamed Alcaligenes organism, ATCC 31555, grows quite well on NA agar, with good colonial morphology. The incubation temperature is 30° C. The organism produces a yellow pigment.

B. Seed Preparation

Flask seeds are prepared in YM broth incubated at 30° C. for 24 hours, then used to inoculate seed medium which is the same as final fermentor medium. A 5% inoculum is used for a 14 L fermentor.

C. Final Fermentor Medium

The following medium gives acceptable results in the 14 L fermentor and can be used for larger scale 20 L and 70 L fermentors:

| Glucose | 3.0% |
|---|---|
| $K_2HPO_4$ | 0.05% |
| Promosoy | 0.05% |
| $NH_4NO_3$ | 0.09% |
| $MgSO_4 7H_2O$ | 0.01% |
| $Fe++$ | 1 ppm |
| HoLe salts | 1 ml/L |

The pH is controlled between 6.5 and 7.5. At 0 hours, pH is 7.3 and residual carbon source was measured to be 3.07%. After 25.5 hours, pH was 7.0 and beer viscosity measured 2350. After 63.5 hours, pH was 6.3 and beer viscosity 3950, and the reaction is terminated by adding 4% isopropanol.

HoLe salts are a trace element solution containing tartrate, magnesium molybdate, $CoCl_3$, $ZnCl_2$, $CuCl_2$, boric acid, manganese chloride and ferrous sulfate.

The initial agitation and aeration rates were 400 rpm and 3 L/M, respectively. The aeration remained constant throughout the fermentation. The agitation was increased as necessary during the fermentation to ensure good mixing. Maximum agitation was 1600 rpm.

When a low calcium product is desired, the medium above is used with deionized water.

D. Broth Adjustment

During this stage, 0.2% calcium propionate is added to the broth. The fermentation broth is adjusted to a pH of 11-11.5 with 45% KOH, followed by heating at 210° F. for 5 minutes.

E. Recovery

Good fibers are produced under precipitation conditions giving 58-62% spent IPA.

F. Drying

Product is recovered after drying with rotary air dryers.

After drying, the product is milled according to standard milling procedures. Target mesh size varies according to desired product characteristics. For example, larger mesh size material, e.g. 80 mesh, is preferred for transport of the material using conventional dry material handling systems. Smaller mesh size material, e.g. 140 mesh, is preferred for enhanced rapid hydration performance. In all cases, however, the gum produced according to the described procedure, using described fermentation broth pH adjustment and subsequent heating steps, possesses rapid hydration characteristics as compared to conventionally prepared welan gum produced according to the procedure described in U.S. Pat. No. 4,342,866.

Measurements of the gum of the present invention in 2% KCl show excellent viscosity development, with excellent NaCl stability and maintenance of viscosity up to at least 300° F.; slight gelation of gum is observed in 2% KCl.

Cement compositions which can be made with the subject rapidly hydrating welan gum comprise cement, fine and/or coarse aggregate, and other optional additives used for various purposes by those skilled in the art. Various types of cements, as well as additives, are described below.

A typical composition for forming a cubic yard of concrete includes about 400-800 lbs. cement; about 120-480 lbs. of water, preferably 0.3-0.6 weight fraction based on weight of cement used; about 1200-4000 lbs. of fine and/or coarse aggregate, preferably 1:3-5 weight ratio of cement: fine and/or coarse aggregate; 0.1-2 lbs. rapidly hydrating welan gum of the present invention, and other optional desirable additives.

Cement compositions of the present invention are prepared using a procedure whereby a portion of the cement powder, optionally with other dry ingredients, is dry-blended with rapidly hydrating welan gum prior to addition to a mixture of cement, water, and fine and/or coarse aggregate. The dry-blend comprises the total amount of rapidly hydrating welan gum to be added and an amount of cement approximately equal to 5 to 20 times by weight the amount of rapidly hydrating welan gum to be added.

In one example, 1 lb. of rapidly hydrating welan gum is combined with 10 lbs. of cement to form a dry-blend. 560 lbs. of dry cement is mixed together with 275 lbs. of water, 1970 lbs. coarse aggregate and 1145 lbs. of fine aggregate, for a period of time, to distribute the cement and aggregate and begin hydration. Thereafter, the gum and cement dry blend is added.

Cement compositions include hydraulic cements, i.e., finely ground and calcined calcium silicates and calcium aluminates which when mixed with water react to form a hard, rock-like mass. Cement is e.g. portland cement, portland pozzolan cement (containing 15-40% pozzolan) blast furnace slag cement, slag cement (containing blast furnace slag and hydrated lime), masonry cement (e.g., adhesive mortars), construction concrete (containing sand and aggregate), oilfield cement (i.e., cements with retarders to prevent rapid setting so that they may be used at high temperatures and pressure environments of deep wells), aluminous cement (containing high amounts of calcium aluminates), expansive cements (containing high sulfate and alumina concentrations and which expand on hardening), air entrained cement (containing compounds which retain air bubbles and thus yield frost- and chemical-resistant concretes), lightweight concrete (containing low density materials such as furnace clinker, pumice, foamed slag, fly ash, gas, wood, etc.) heavy concrete (containing dense material such as barite, iron ore (i.e., illmenite or hematite), steel, etc.), and low heat concrete (with modified compositions that minimize heat generation during the setting process).

Oilfield cements are basically the same as those used in construction (i.e., portland cement). The American Petroleum Institute has set specifications for oilfield cements. These as classified as "A" through "H", and "N", all of which are useful in compositions of this invention.

Cement additives in oilfield cements are materials mixed in the slurry for reducing or increasing density, increasing volume at reduced unit cost, accelerating or retarding slurry thickening time, increasing strength, preventing loss of whole cement slurry, increasing or improving the durability, decreasing water loss from the slurry, and increasing or decreasing the viscosity of the cement slurry.

It is a purpose of the invention to use rapidly hydrating welan gum for controlling water loss from cement slurries and as a suspending agent. The gum increases workability of cement compositions. The increased workability is conveniently achieved by dry blending rapidly hydrating welan gum with a portion of cement and then adding the gum/cement blend to a cement/water pre-mix. Incorporation of rapidly hydrating welan gum in this fashion eliminates the need for prehydrating the gum prior to a cement/sand/water mix and avoids interference with the hydration reaction of cement and water.

It improves the ability of cement slurries to be easily placed in crowded area such as around re-inforcing bars without aggregate settling.

Cement slurries containing rapidly hydrating welan gum show more uniform density as the curing process proceeds. The suspension properties of the gum keep the slurry more uniform, yielding less aggregate settling and less free water on the surface of the slurry.

Cement additives which are useful in compositions of this invention include mineral admixtures, accelerators, retarders, fluid loss reducers, dispersants, extenders and loss circulation materials, antifoam agents, and weighting materials.

Mineral admixtures include silica fume, fly ash, blast furnace slag or fibers.

Accelerators include calcium chloride, sodium silicate (Diacel A), sodium chloride (salt), ammonium chloride ($NH_4Cl$), or combinations or solutions of these salts.

Retarders include calcium or sodium lignosulfonates or other lignin derivatives, borax compounds, CM HEC (carboxymethylhydroxethylcellulose), sodium or calcium gluconates, and sugars.

Fluid loss reducers include bentonite, high, medium and low viscosity HEC, polyethylene imines and amines, long chain alcohols, CM HEC, polyvinyl pyrrolidones, and fine inorganic solids (such as talc).

Dispersants include sodium citrates, sodium napthalene sulfonates, lignin and lignin derivatives to reduce viscosities of cement slurries and to aid in fluid loss control by dispersing the particles in the slurry.

Extenders and loss circulation materials include pozzalons, asphalts, gilsonites, bentonite, diatomaecous earth, and various materials to plug passages where loss of whole cement occurs.

Antifoam agents include long chain alcohols such as octanols, stearates and their salts.

Weighting materials include barite, hematite, and illmenite to increase the density of cement slurries.

The cement compositions of this invention can be conveniently prepared by adding rapidly hydrating welan gum in dry form to the rest of the compositions. The invention is further defined by reference to the following preparations and examples, which are intended to be illustrative and not limiting.

EXAMPLE 2

A cubic yard of concrete was prepared according to the procedure of the present invention. To prepare a suitable cement slurry, 6 lbs. of API type G cement was dry blended with 0.3 lbs. 140 mesh rapidly hydrating welan gum prepared according to the procedure described in Example 1. The dry blend was added to a cement/water aggregate pre-mix, containing 560 lbs. cement, 1800 lbs. aggregate, and 283 lbs. water, to produce a homogeneous, smooth soft cement slurry, the viscosity of which increased with increasing gum concentration and with time.

EXAMPLE 3

A cement slurry was prepared according to the procedure of Example 2, except that Portland type A cement was used instead of API type G cement, and 0.5 to 0.8% Lomar PW dispersant was added to the gum/cement dry blend. The resulting slurry produced a homogeneous, smooth soft cement slurry.

EXAMPLE 4 (Control)

Following the procedure of Example 3, but substituting welan gum prepared according to the procedure described in U.S. Pat. No. 4,342,866 for rapidly hydrating welan gum, cement, water, dispersant and gum were mixed. Because the gum did not hydrate properly, a low-viscosity, non-homogeneous material containing visually distinguishable gel balls was obtained.

EXAMPLE 5

A slurry containing H cement, 0.7% dispersant, 46% water and 0.3% rapidly hydrating welan gum (all based on dry weight), according to the procedure described in Example 2, was prepared. A smooth, soft, homogeneous cement slurry was obtained.

EXAMPLE 6

Another Fermentation and Recovery Procedure for Producing Rapidly Hydrating Welan Gum A. Culture Maintenance The unnamed Alcaligenes organism, ATCC 31555 grows quite well on nutrient agar. The incubation temperature is 30° C. The organism produces a yellow pigment.

B. Seed Preparation

Flask seeds are prepared in YM broth incubated at 30° C. for 24 hours with shaking. Fresh YM broth seeds are then started using a 1% inoculum. After 24 hours incubation at 30° C. with shaking these YM seeds are used to inoculate a one-gallon fermentor containing a seed medium which is the same as the final fermentor medium except that it contains 0.5% $K_2HPO_4$. The inoculum size is 6.7% and the fermentation temperature is 30° C. The air flow rate is one L/M and the agitation is set at 400 RPM. At 25 hours this seed was used to start a 30 L fermentor with an inoculum size of 5%.

C. Final Fermentor Medium

The following medium gives acceptable results in the 30 L fermentor and can be used for larger scale fermentors such as 70 L.

| | |
|---|---|
| Glucose | 3.0% |
| $K_2HPO_4$ | 0.13% |
| Promosoy | 0.25% |
| $NH_4NO_3$ | 0.03% |
| $MgSO_4.7H_2O$ | 0.05% |
| $Fe_4.7H_2O$ | 10 ppm |
| Antifoam (Hodag K-21) | |
| Tap Water | |

The pH is controlled between 6.5 and 7.5. At 0 hours, the residual carbon source was measured to be 3.08%. At 69 hours, the pH was 6.55 and the beer viscosity was 42,500 cP.

The initial agitation and aeration rates were 300 rpm and 5 L/M, respectively. The eaction rate was increased to 10 L/M at 20 hours and then remained constant through the fermentation. The agitation was increased to 700 RPM (maximum) at 20 hours.

When a low calcium product is desired, the medium above is used with deionized water.

D. Broth Adjustment

During this stage, 0.2% calcium propionate is added to the broth. The fermentation broth is adjusted to a pH of 11-11.5 with 45% KOH, followed by heating at 210° F. for 5 minutes.

E. Recovery

Good fibers are produced under precipitation conditions giving 58-62% spent IPA.

F. Drying

Product is recovered after drying with rotary air dryers.

After drying, the product is milled according to standard milling procedures. Target mesh size varies according to desired product characteristics. For example, larger mesh size material, e.g. 80 mesh, is preferred for transport of the material using conventional dry material handling systems. Smaller mesh size material, e.g. 140 mesh, is preferred for enhanced rapid hydration performance. In all cases, however, the gum produced according to the described procedure, using described fermentation broth pH adjustment and subsequent heating steps, possesses rapid hydration characteristics as compared to conventionally prepared welan gum produced according to the procedure described in U.S. Pat. No. 4,342,866.

This product was demonstrated to have hydration and solution properties similar to the sample described in the Example 1.

EXAMPLE 7

A rapidly hydrating welan gum is prepared according to the procedure of Example 1 wherein during recovery the pH is controlled at 11 and the temperature is maintained at 170° F. for 5 minutes. The dried gum is milled to 140 mesh size.

EXAMPLE 8

A rapidly hydrating welan gum is prepared according to the procedure of Example 1 wherein during recovery the pH is controlled at 11 and the temperature is maintained at 210° F. for 5 minutes. The dried gum is milled to 80 mesh size.

EXAMPLE 9

A rapidly hydrating welan gum is prepared according to the procedure of Example 1 wherein during recovery the pH is controlled at 11, the temperature is maintained at 210° F. for 5 minutes, and the broth is sheared through a high shear mixer. The dried gum is milled to 80 mesh size.

EXAMPLE 10 a rapidly hydrating welan gum is prepared according to the procedure of Example 1 wherein during recovery the pH is controlled at 11.5 and the temperature is maintained at 170° F. The dried gum is milled to 80 mesh size.

EXAMPLE 11

A rapidly hydrating welan gum is prepared according to the procedure of Example 1 wherein during recovery the pH is controlled at pH 11.5, the temperature is maintained at 170° F. and the broth is sheared through a high shear mixer. The dried gum is milled to 80 mesh size.

EXAMPLE 12

A rapidly hydrating welan gum is prepared according to the procedure of Example 1 wherein during recovery the pH is controlled at 11 and the temperature is maintained at 211°-215° F. The dried gum is milled to 80 mesh size.

EXAMPLE 13

Control welan gum is prepared according to the procedure described in Example 1 with the exception that Step D ("Adjustment") is not performed. The procedure includes step C, followed by heating of the broth to 170° F. for 5 minutes, followed by Step E. Three different batches were prepared (13a, 13b and 13c) and each was milled to 40 mesh size and 150 mesh size.

EXAMPLE 14

Hydration Test

In order to determine hydration characteristics for rapidly hydrating welan gums produced in accordance with the procedure of the invention, the gums were combined with polyethylene glycol and viscosity measurements were made using a Solution Rate Tester.

The tester can measure the hydration rate of polymer solutions by monitoring the torque on a beaker as it is being stirred at a constant speed. As the gum dissolves and the viscosity increases, beaker torque increases. While factors such as turbulence, non-laminar flow, pseudoplasticity, etc. prevent a direct correlation of torque reading and viscosity, plotting torque against time provides a good indication of viscosity development.

Material is tested at 0.5 wt. % in synthetic tap water for 15 minutes at 600 rpm in a Solution Rate Tester. Samples are added in a polyethylene glycol slurry at a ratio of 3 parts glycol to 1 part gum.

Viscosities are measured after 15 minutes of mixing plus 1 hour rest and after shearing for 1 minute in a blender and 18 hours rest. Ideally, the blended solution should be de-aerated before the viscosity is measured, or a defoamer added to the gum solution before blending. 3 grams of glycol and 1 gram of dry gum are weighed into a 10 ml beaker. The slurry is mixed with a small spatula by hand for about 30 seconds. 2.6 grams of the slurry are then placed into a 5 cc syringe, and the syringe tip cut off to prevent shearing. 127.4 grams of synthetic tap water is weighed into the stainless steel beaker used with the Solution Rate Tester.

| Sample (Example #) | Brookfield LVT, cP, 3 rpm | | % Final Viscosity | Minutes to reach 90% torque |
|---|---|---|---|---|
| | 1 hour | blended | | |
| 7 | 14,600 | 15,800 | 92.4 | 1.83 |
| 8 | 6,900 | 6,650 | 100 | 2.16 |
| 9 | 7,200 | 6,900 | 100 | 2.30 |
| 10 | 7,800 | 8,000 | 97.5 | 9.05 |
| 11 | 9,300 | 9,700 | 95.9 | 7.83 |
| 12 | 7,250 | 6,100 | 100 | 2.33 |
| 13a (40 mesh) | 10,000 | 12,000 | 83.3 | 33.28 |
| (150 mesh) | 9,200 | 9,600 | 95.8 | 11.79 |
| 13b (40 mesh) | 10,000 | 13,400 | 74.6 | 18.64 |
| (150 mesh) | 8,400 | | 100 | 10.58 |
| 13c (40 mesh) | 8,550 | 14,000 | 62.9 | 23.48 |
| (150 mesh) | 8,400 | 13,000 | 64.6 | 10.76 |

Utility

In addition to the uses described above, uses for the rapidly hydrating gum of the present invention include use as an antiwashout admixture for the construction and repair of structures underwater, production of a fluid, non-bleeding grout for post-tensioned structures, improvement of bond between reinforcing steel and concrete, shotcrete, lightweight concrete, air entranced concrete, oilfield cements, fiber containing concrete, extruded concrete products, precast products as well as general use in grouts. Concentrations of the gum required for adequate functionality vary with the application.

What is claimed is:

1. A rapidly hydrating welan gum heteropolysaccharide prepared according to the process steps of:
    a) inoculating a suitable aqueous nutrient media with Alcaligenes bacterial strain ATCC 31555;
    b) aerobically fermenting the bacteria at a pH of between about 6.5 and 7.5;
    c) adding calcium propionate to the broth, adjusting the pH to about 10.5-12.5, and heating the fermentation broth at a temperature of about 170° F.-230° F. for about 3-20 minutes;
    d) precipitating the heteropolysaccharide from the fermentation media;
    e) drying the precipitate; and
    f) milling the dried precipitate.

* * * * *